July 14, 1959 W. ZOMBORY ET AL Plant Pat. 1,851
DIANTHUS CARYOPHYLLUS PLANT
Filed Nov. 12, 1958
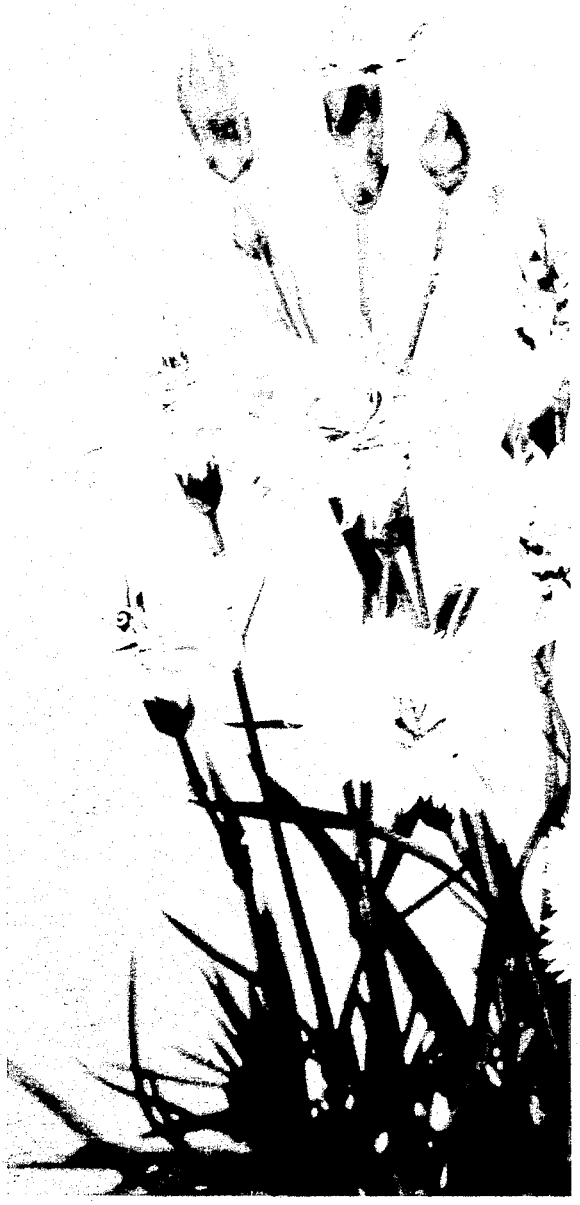
Inventors
William Zombory and
Sophie Zombory
By: Robb & Robb
Attorneys United States Patent Office Plant Pat. 1,851
Patented July 14, 1959

1,851

DIANTHUS CARYOPHYLLUS PLANT

William Zombory and Sophia Zombory, Detroit, Mich., assignors to Jackson & Perkins Company, Newark, N.Y., a corporation of New York Application November 12, 1958, Serial No. 773,532

1 Claim. (Cl. 47—60)

The present invention relates to a new and distinct variety of *Dianthus caryophyllus* plant, which was originated by us by crossing the variety "Dianthus Irene" (Plant Patent No. 747) with an unnamed and unpatented seedling of *"Dianthus allwoodii"* (unpatented).

The primary objective of this breeding was to produce a new variety of Dianthus which bears fragrant and colorful flowers without the calyx-splitting habit that is characteristic of the variety "Irene." This objective was fully achieved along with other desirable improvements, as evidenced by the following unique combination of outstanding characteristics of our new variety which distinguish it from its parents as well as from all other varieties of which we are aware:

(1) A compact plant habit, with Forest Green foliage;

(2) Early blooming, winter-hardy and very long-lived habits;

(3) Repeating blooming habit in the fall;

(4) Neat, compact, and non-splitting form of the flowers;

(5) A distinctive Cameo Pink, lightly overcast with Rose Pink, general color tonality of the flowers; and (6) A heavy flower fragrance.

Our new variety has many characteristics that are similar to those of its parent "Irene," but it is a decided improvement, particularly from the standpoint of its flower form and general appearance. The neatness and non-splitting habit of the flowers are especially apparent. In the geographical area of upstate New York, the plants are winter-hardy and are very long-lived, and the plants do not develop an open center such as occurs in other varieties, but stays compact at all times and therefore provides unusually good ground cover.

Asexual reproduction of our new variety by cuttings, as performed at Detroit, Michigan, and also at Newark, New York, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—"Dianthus Irene."

*Pollen parent.*—An unnamed seedling of *"Dianthus allwoodii."*

Blooming season: Starts blooming the first year from cuttings, with bloom extending from 5 to 6 weeks annually in June, and again in the fall.

*Plant*

Growth: Stout; erect; smooth cespitose perennial; compact; sends up flowering shoots the first year.

Leaves: Many bottom leaves in tufts; from 2 inches to 2½ inches long; thick; narrow. Color—Forest Green, Plate 17.

Flower stems: From 15 inches to 18 inches long; obscurely angled; nodes prominently swollen and covered in the leaf sheath; forked towards the top so that it is usually 3 or 5-flowered, but most commonly 4-flowered. Color—Chromium Green, Plate 32.

*Flower*

Borne: Mostly on own-branched stalks, but some of the laterals nearly sessile.

Size: From 1½ inches to 2 inches in diameter at first, with later flowers on laterals from 1 inch to 1½ inches in diameter.

Petals: Average 25 in number in fully grown flowers; about ½ inch in width at the widest point; up to 1½ inches long; prominent serrations on edges; not bearded in the throat, but have a small Amaranth Purple, Plate 12, blotch at the beginning of the throat.

Color: Cameo Pink, Plate 26, lightly overcast with Rose Pink, Plate 12, with blotch at throat Amaranth Purple, Plate 12; Claw White, Plate 53, blended in with Pale Glass Green, Plate 31.

Calyx: Cylindrical, somewhat narrowing toward apex; about ¾ inch long; small teeth; erect; does not split at any time. Color—teeth of Biscay Green, Plate 17, with lower half of calyx lightly overcast with Indian Lake, Plate 27.

Bracts: 4 in number; small. Color—Bice Green, Plate 17.

Stamens: From 10 to 12 in number; about 1 inch long. Color—White, Plate 53.

Anthers: Color—Pale Lilac, Plate 37.

Ovary: Small; oval.

Fragrance: Very sweet and strong. Nature—clove perfume (quite different from "Dianthus Irene").

We claim:

A new and distinct variety of *Dianthus caryophyllus* plant, substantially as herein shown and described, characterized particularly as to novelty by the unique combination of a compact plant habit, with Forest Green foliage, early blooming, winter-hardy and very long-lived habits, a repeating blooming habit in the fall, neat, compact and non-splitting form of the flowers, a distinctive Cameo Pink, lightly overcast with Rose Pink, general color tonality of the flowers, and a heavy flower fragrance.

No references cited.